United States Patent
Lesma

(10) Patent No.: US 6,906,187 B2
(45) Date of Patent: Jun. 14, 2005

(54) MANUFACTURE OF CEFALOSPORINS AND INTERMEDIATES

(75) Inventor: Giordano Lesma, Milan (IT)

(73) Assignee: Miat S.p.A., Milan (IT)

( * ) Notice: Subject to any disclaimer, the term of this patent is extended or adjusted under 35 U.S.C. 154(b) by 78 days.

(21) Appl. No.: 10/374,723

(22) Filed: Feb. 27, 2003

(65) Prior Publication Data

US 2004/0176590 A1 Sep. 9, 2004

(51) Int. Cl.[7] ................... C07D 501/36; C07D 501/59; C07D 501/22

(52) U.S. Cl. ..................... 540/222; 540/227

(58) Field of Search ................ 540/227, 222

(56) References Cited

U.S. PATENT DOCUMENTS 4,327,210 A * 4/1982 Montavon et al. .......... 540/227
4,622,318 A * 11/1986 Takaya et al. .............. 540/227

* cited by examiner

*Primary Examiner*—Mark L. Berch
(74) *Attorney, Agent, or Firm*—Nixon & Vanderhye P.C.

(57) ABSTRACT

There is described a process for the preparation of 3-disubstituted cepham-4-carboxylic acid derivatives of formula I (I)

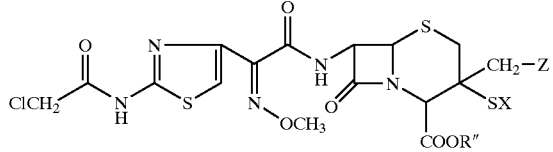

wherein R" is 4-methoxybenzyl, X is the residue of a thioether and Z is a residue of a nucleophilic compound, such as 2-furoylthio, acetoxy or 1,2,5,6-tetrahydro-2-methyl-5,6-dioxo-1,2,4-triazin-3-ylthio, by reaction of a functional derivative of α-(2-chloroacetamido)thiazol-4-yl-α-methoxyiminoacetic acid with 7β-amino-3-methylenecepham-4-carboxylic acid 4-methoxybenzyl ester, subsequent treatment of the obtained 4-methoxybenzyl 7β-[α-(2-chloroacetamido)thiazol-4-yl-α-methoxyimino]acetamido-3-methylenecepham-4-carboxylate with a S-chloromercaptan of formula X—S—Cl, such as methanesulfenyl chloride, and final treatment of the corresponding 4-methoxybenzyl 7β-[α-(2-chloroacetamido)thiazol-4-yl-α-methoxyimino]acetamido-3-thio-3-chloromethylcepham-4-carboxylate thus obtained of formula V (V)

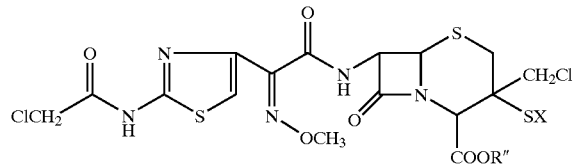

wherein R" and X are as defined above, with a compound of formula M-Z, in which M is an alkaline metal or a hydrogen atom and Z is as defined above. These novel intermediates may be converted into the corresponding 3-cephem derivatives by oxidative cleavage of the mercaptan X—SH. By suitable deprotection, these 3-cephem derivatives afford cephalosporins such as ceftiofur, cefotaxime and ceftriaxone.

19 Claims, No Drawings

MANUFACTURE OF CEFALOSPORINS AND INTERMEDIATES

OBJECT OF THE INVENTION

The present invention concerns novel 7β-acylamido-3-thio-3-halomethylcepham-4-carboxylic acid derivatives, a process for their preparation through new intermediates and for the subsequent replacement of the halogen atom of said 7β-acylamido-3-thio-3-halomethylcepham-4-carboxylic acid derivatives by the residue of a nucleophilic compound to obtain corresponding precursors of 7β-acylamido-3-(substituted)methyl-3-cephem-4-carboxylic acid derivatives.

BACKGROUND OF THE INVENTION

Many semisynthetic, therapeutically used cephalosponrns generally consist of 7β-acylamido-3-(substituted)methyl-3-cephem-4-carboxylic acid derivatives in which the 3-methyl group is substituted with the residue of a nucleophilic compound and the acyl group is a variously 2-mono-, 2,2-di- or 2,2,2-tri-substituted acetic acid. Mainly, the residue of the nucleophilic compound is a methoxy; acetoxy; carbamoyl; an optionally substituted heterocycle radical, including tertiary ammonium heterocycles forming an inner salt with the cephem-4-carboxylic acid, such as 5-methyltetrazol-2-yl, 1-pyridinio, 4-carbamoyl-1-pyridinio, 2-sulfoethyl-1-pyridinio, 5,6,7,8-tetrahydro-1-quinolinio, 1-cyclopentano[b]pyridinio, 1H-imidazo [1,2-b]-4-pyridazinio, 5-metyl-1-(2-hydroxyethyl)-3-imidazolio, 1-quinuclidinio, 4-carbamoyl-1-quinuclidinio, 1-methyl-1-pyrrolidinio; or a mercapto group substituted with a furyol, thenoyl group or with an optionally substituted heterocycle radical such as 1-methyltetrazol-5-yl, 1-sulfomethyltetrazol-5-yl, 1-(2-dimethylaminoethyl)tetrazol-5-yl, thiazol-2-yl, 5-carboxymethyl-4-methylthiazol-2-yl, 5-methyl-1,3,4-thiadiazol-2-yl, 1 H-1,2,3-triazol-4-yl, 1H-1,2,4-triazol-3-yl, 5-methyl-1,3,4-thiadiazol-2-yl, 1,2,5,6-tetrahydro-2-methyl-5,6-dioxo-1,2,4-triazin-3-yl. Mainly, the acyl group is an optionally substituted phenylacetyl, α-(optionally N-substituted)aminophenylacetyl, α-sulfophenylacetyl, α-(optionally O-substituted)hydroxyphenylacetyl (particularly mandeloyl), cyanoacetyl, thienylacetyl, trifluormethylthioacetyl, cyanomethylthioacetyl, (3,5-dichloro-4-oxo-4H-pyrid-1-yl)acetyl, tetrazol-1-ylacetyl, (2-aminothiazol-4-yl)acetyl, 2-(2-aminothiazol-4-yl)-2-(optionally O-protected)oxyiminoacetyl, 2-(5-aminol,2,4-thiadiazol-3-yl)-2-(optionally O-protected)oxyiminoacetyl, S-cysteinylacetyl, thien-2-ylacetyl.

More particularly, the so-called "third-generation-cephalosporins" generally consist of 3-methyl-3-cephem-4-carboxylic acid derivatives substituted in the 7β-position by an α-(2-aminothiazol-4-yl)-α-hydroxyiminoacetamido group, in which the hydroxy group is free or On-substituted with an alkyl group, optionally substituted by a carboxy group, and substituted on the methyl group in the 3-position with the residue of a nucleophilic compound.

The above mentioned third-generation-cephalosporins have been described for the first time in the published German application DE 2556736 (corresponding to U.S. Pat. No. 5,583,216) and, principally, are compounds encompassed by the general formula A

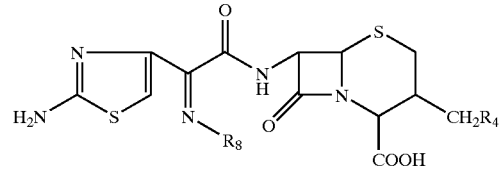

(A)

wherein $R_4$ is the residue of a nucleophilic compound and $R_5$ is a hydroxy group which may be protected, including their pharmaceutically acceptable esters, the respective salts and the relative solvates Among these third-generation-cephalosporins, the 7β-[α-(2-aminothiazol-4-yl)-α-hydroxyimino]acetamido-3-methyl-3-cephem-4-carboxylic acid derivatives of formula A, in which $R_5$ is methoxy and $R_4$ is a 2-furoylthio group (ceftiofur), an acetoxy group (cefotaxime) or a,1,2,5,6-tetrahydro-2-methyl-5,6-dioxo-1,2,4-triazin-3-ylthio group (ceftriaxone) are particularly interesting compounds.

DESCRIPTION OF THE PRIOR ART

The 7β-[α-(2-aminothiazol-4-yl)-α-hydroxyimino]acetamido-3-methyl-3-cephem-4-carboxylic acid derivatives in which the 3-methyl group is substituted with the residue of a nucleophilic compound are prepared according to the general method, described in DE 2556736 and U.S. Pat. No. 5,583,216, which comprises introducing the α-(2-aminothiazol-4-yl)-α-hydroxyiminoacetyl radical, wherein the hydroxy and amino groups are suitably protected, onto the amino group of a 7β-amino-3-methylcephem-4-carboxylic acid in which the Methyl group is substituted with the residue of a nucleophilic compound.

The 3-$CH_2R_4$ substituent in the formula A above is easily derivable from cephalosporins produced by fermentation and the meaning of $R_4$ is illustrated for example in U.S. Pat. No. 5,583,216.

Since the appearance of the document DE 2556736, in 1976, the sole valid process suitable for the preparaton of the cephalosporins of formula A had been that described in said document Recently, processes disclosing the introduction of a precursor of the α-(2-aminothiazol-4-yl)-α-hydroxyiminoacetyl radical onto the amino group of a 7β-amino-3-methyl-3-cephem in which the methyl group is substituted with the residue of a nucleophilic compound have been disclosed (see EP 842937 A2 and US 2002/0128469 A1).

Finally, T. Aoki et al. (Tetrahedron 1983, 34/15, 2515-2556—in particular pages 2520–2525) disclose the synthesis of diphenylmethyl 7β-(2-thienylacetamino)-3-(1-methyl-1H-tetrazol-5-yl)thiometyl-3-cephem-4-carboxylate, which involves the preparation of diphenylmethyl 7β-(2-thienylacetamino)-3-(1-methyl-1H-tetrazol-5-yl)-3-methylthiocepham-4-carboxylate via the corresponding 3-methylthio-3-chloromethylcepham analog and the reaction of said diphenylmethyl 7β-(2-thienylacetamino)-3-(1-methyl-1H-tetrazol-5-yl)-3-methylthiocepham-4-carboxylate with m-chloroperbenzoic acid in order to remove methylmercaptan and form a 3-(1-methyl-1H-tetrazol-5-yl)-3-cephem structure via the corresponding 1-oxide. However, the method described by Aoki et al. is not transposable to the preparation of third-generation-cefalosporins because the reactants employed affect the amino group which is present on the thiazole ring and is sensitive thereto.

To make the terminology uniform and the text more understandable, in the present description meanings and conventional expressions, in singular or plural form, will be used. In particular, unless otherwise specified:
the term "7β-cephem" designates the radical of formula (a)

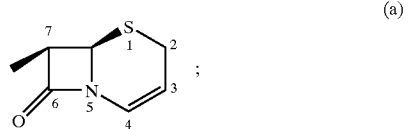

the term "3-methylenecepham" or "3-exomethylenecepham" means the 3-methylene-3,4-dihydro-7β-cephem radical of formula (b), the "cepham" having the structure (c)

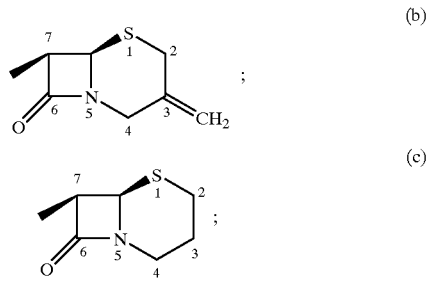

the formulas drafted herein refer to 7β-substituted derivatives as referred to for the above 7β-cephem and 3-methylenecepham radicals, the protected carboxyl group which is normally present in the 4-position of the 3-methylenecepham (b) or cephem radicals being indifferently in the α or β configuration;
the term "3-thio" in the 3-thio-3-(substituted)methylcepham structure generically designates a sulfur atom attached to the 3-position of the cepham moiety and substituted with an inert organic radical X forming a thioether, as defined hereinbelow;
the oxyimino group which is present in the formula I above and in the other formulas hereinbelow is in the syn configuration.

SUMMARY OF THE INVENTION

According to the method disclosed in DE 2556736 and also in the lastly published documents EP 842937 A2 and US 2002/0128469 A1, the preparation of the compounds of formula A always occurs by introduction of the α-(2-aminothiazol-4-yl)-α-hydroxyiminoacetyl radical, or of a precursor thereof, onto the amino group of a 7β-amino-3-methylcephem-4-carboxylic acid in which the methyl group is always substituted with the residue of a nucleophilic compound.

It has now been found that, starting from easily available starting materials, it is possible to prepare a precursor of the above-mentioned cephalosporins of formula A, in which $R_5$ is methoxy and $R_4$ is 2-furoylthio, acetoxy or 1,2,5,6-tetrahydro-2-methyl-5,6-dioxo-1,2,4-triazin-3-ylthio, by introducing the α-(2-aminothiazol-4-yl)-α-methoxyiminoacetyl radical onto the amino group of 4-methoxybenzyl 7β-amino-3-methylenecepham-4-carboxylate and converting the methylene group into a precursor of the 7β-amino-3-methylcephem-4-carboxylic acid in which the methyl group is substituted with a 2-furoylthio, acetoxy or 1,2,5,6-tetrahydro-2-methyl-5,6-dioxo-1,2,4-triazin-3-ylthio group. In particular, it has been found that, by reacting a functional derivative of α-methoxyimino-α-[2-(2-chloroacetamido)thiazol-4-ylacetic with 4-methoxybenzyl 7β-amino-3-methylenecepham-4-carboxylate, treating the 4-methoxybenzyl 7β-[-α-2-chloroacetamido)thiazol-4-yl-α-methoxyimino]acetamido-3-methylenecepham-4-carboxyate thus obtained with methyl sulfenyl chloride, and treating the 4-methoxybenzyl 7β-[α-(2-chloroacetamido)thiazol-4-yl-α-methoxyimino]acetamido-3-thio-3-chloromethylcepham-4-carboxylate with an alkaline metal salt of 2-thiofuroic acid, of acetic acid or of 3-mercapto-2-methyl-5,6-dioxo-1,2,4-triazine-3-thione a 4-methoxybenzyl 7β-[α-(2-chloroacetamido)thiazol-4-yl-α-methoxyimino]acetamido-3-methylthio-3-(substituted)methylcepham-4-carboxyate is obtained. A specific embodiment of the process is depicted in Scheme 1 below, in which X is an inert organic group, R" is 4-methoxybenzyl and Z is the residue of a nucleophilic compound selected from the group consisting of the 2-furoylthio, acetoxy and 1,2,5,6-tetrahydro-2-methyl-5,6-dioxo-1,2,4-triazin-3-ylthio radicals. This compound is a new precursor of third-generation-cephalosporins which may be converted into them according to methods well known in the cephalosporin chemistry. As far as the applicant know, literature does not disclose methods allowing the introduction of the α-(2-aminothiazol-4-yl)-α-methoxyiminoacetyl radical onto the amino group of a precursor of a 7β-amino-3-methylcephem-4-carboxylic acid in which the methyl group is substituted with the residue of a nucleophilic compound

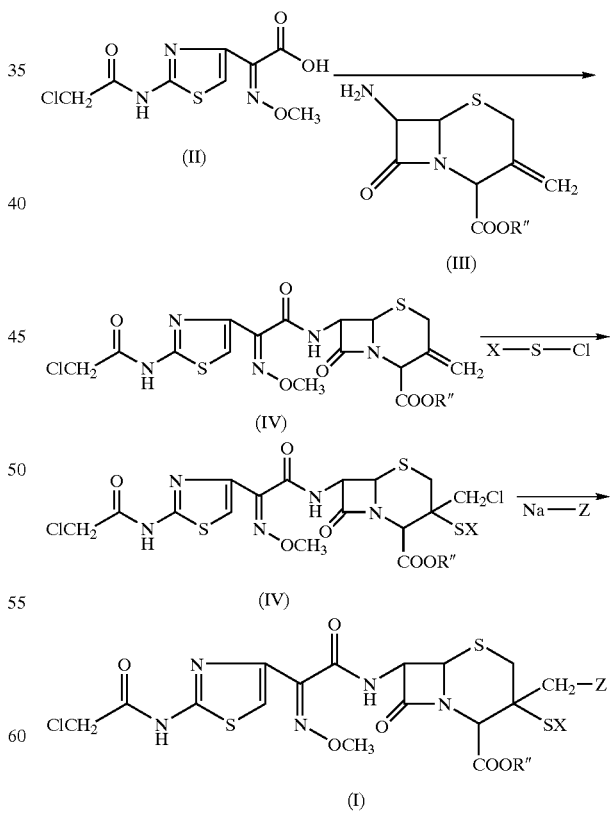

It has also been surprisingly found that, by submitting the 4-methoxybenzyl 7β-[α-(2-chloroacetamido)thiazol-4-yl-α-methoxyimino]acetamido-3-methylthio-3- chloromethylcepham-4-carboxylate of formula V (X=CH₃) of Scheme 1 to the action of a peracid such as m-chloroperbenzoic acid, a selective elimination of methylmercaptan occurs with concurrent formation of the 3-chloromethyl-3-cephem structure without affecting the sulfur atom in 1-position of said 3-cephem structure, thus allowing the preparation of the corresponding 3-chlorometyl-3-cephem-4-carboxylic acid 4-methoxybenzyl ester in good yields and in pure state. Conversely, the sulfoxide forms when the treatment with the peracid is made on compound I.

Thus, by the action of the peracid, the compound V (X=CH₃) is directly converted into the new 4-methoxybenzyl 7β-[α-(2-chloroacetamido)thiazol-4-yl-α-methoxyimino]acetamido-3-chloromethyl-3-cephem-4-carboxylate of formula VI (VI)
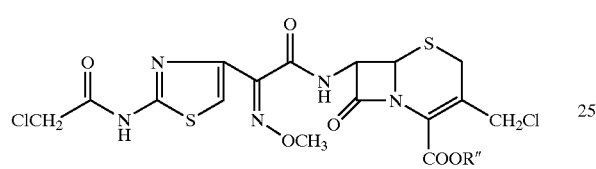

wherein R" is as defined above, which may be reacted with a compound M-Z, wherein Z is as defined above and M is an alkaline metal atom and converted into the 4-methoxybenzyl ester of ceftiofur, cefotaxime or ceftriaxone, N-protected with the chloroacetyl group.

By submitting compound I (X=CH₃) to the action of a peracid, said compound of formula I is converted into the corresponding 4-methoxybenzyl 7β-[α-(2-chloroacetamido)thiazol-4-yl-α-methoxyimino]acetamido-3-(substituted)methyl-3-cephem-4-carboxyate 1-oxide of formula VII.

(VII)
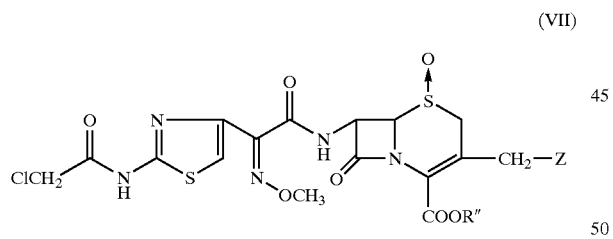

wherein Z and R" are as defined above, which, by reduction with stannous chloride, is converted into the 4-methoxybenzyl ester of ceftiofur, cefotaxime or ceftriaxone, N-protected with the chloroacetyl group.

The term "2-furoylthio" indicates the 2-furanecarbonythio radical, the corresponding free thioacid being referred to as "2-thiofuroic acid".

DETAILED DESCRIPTION OF THE INVENTION

Thus, it is an object of the present invention to provide a process for the preparation of a 3-disubstituted cepham-4-carboxylic acid derivative of formula I (I)
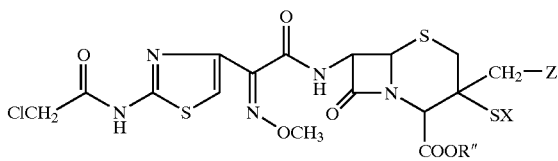

wherein R" is 4-methoxybenzyl, X is the residue of a thioether and Z is the residue of a nucleophilic compound selected from the group consisting of 2-furoylthio, acetoxy and 1,2,5,6-tetrahydro-2-methyl-5,6-dioxo-1,2,4-triazin-3-ylthio radicals, which comprises (i) reacting a functional derivative of α-(2-chloroacetamido)thiazol-4-yl-α-methoxyiminoacetic acid of formula II (II)
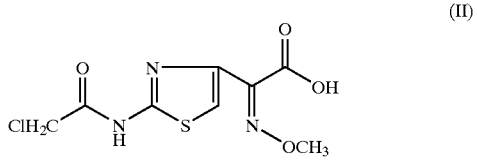

with a 7β-amino-3-mnethylenecepham-4-carboxylic acid derivative of formula III (III)
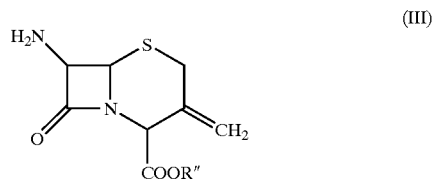

wherein R" is 4-methoxybenzyl, or with an addition salt thereof;

(ii) treating the corresponding 4-methoxybenzyl 7β-[α-(2-chloroacetamido)thiazol-4-yl-α-methoxyimino]acetamido-3-methylenecepham-4-carboxylate thus obtained of formula IV (IV)
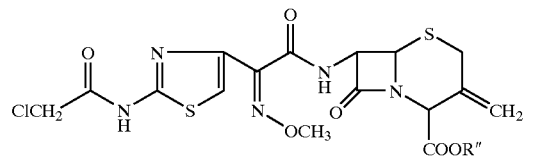

wherein R" is 4-methoxybenzyl, with a S-chloromercaptan of formula X—S—Cl, in which X is as defined above; and (iii) reacting the corresponding 4-methoxybenzyl 7β-[α-(2-chloroacetamido)thiazol-4-yl-α-methoxyimino]acetamido-3-thio-3-chloromethylcepham-4-carboxylate thus obtained of formula V (V)

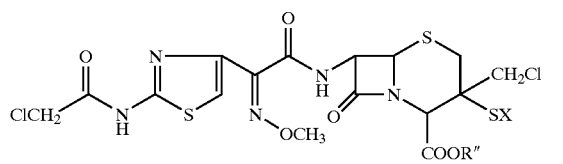

wherein R" and X are as defined above, with a compound of formula M-Z, in which M is an alkaline metal or a hydrogen atom and Z is the residue of a nucleophilic compound, selected from the group consisting of the 2-furoylthio, acetoxy and 1,2,5,6-tetrahydro-2-methyl-5,6-dioxo-1,2,4-triazin-3-ylthio radicals.

According to the present invention, the residue X is an inert organic radical forming a thioether with the sulfur atom to which it is attached, such as a phenyl or benzyl group as well as their analogues substituted on the phenyl radical with, for example, methyl or methoxy groups, or X can be a methyl group, which is a preferred thioether residue.

The functional derivative of the α-(2-chloroacetamido)thiazol-4-yl-α-methoxyiminoacetic acid of formula II used as starting material may be an acid halide thereof, the anhydride, a mixed anhydride, an active ester or the free acid itself, duly activated for example with dicyclohexylcarbodiimide, with mercaptobenzotriazole or with the so-called "BOP reagent", namely the benzotriazol-1-yloxy-tris(dimethylamino)phosphonium hexafluorophosphate. An advantageous functional derivative is the acid chloride which may be obtained by reaction of the free acid with thionyl chloride and may be straightforwardly made to react in situ with the compound of formula III. Another advantageous functional derivative is the mixed anhydride with a sulfonic acid, preferably with p-toluene sulfonic acid, or with a monoester of carbonic acid, preferably with carbonic acid monoethylester, which may be obtained from α-(2-chloroacetamido)thiazol-4-yl-α-methoxyiminoacetic acid and an acid chloride such as p-toluenesulfonyl chloride or ethyl chloroformate and directly made to react in situ with the compound of formula III. The compound II free acid is obtained by introducing the chloroacetyl group onto the amino group of the α-(2-amino)thiazol-4-yl-α-methoxyiminoacetic acid (free acid) as illustrated above.

In step (i), said functional derivative is made to react with the 4-methoxybenzyl 7β-amino-3-methylenecepham-4-carboxylate, as free base or as a salt thereof, for example as hydrochloride, methanesulfonate (mesylate) or p-toluenesulfonate (tosylate). The reaction is carried out according to the classical procedure of the peptide chemistry. In practice and advantageously, the chloride or the mixed anhydride with carbonic acid monoethylester or with p-toluene sulfonic acid of 4-methoxybenzyl α-(2-chloroacetamido)thiazol-4-yl-α-methoxyiminoacetate of formula II, or the free acid in the presence of dicyclohexylcarbodiimide, of mercaptobenzotriazole or of the BOP reagent, is treated in an organic solvent, such as toluene, dichloromethane dioxane or tetrahydrofurane, with the 4-methoxybenzyl 7β-amino-3-methylenecepham-4-carboxylate, as free base or as a salt thereof, such as the hydrochloride, methanesulfonate (mesylate) or p-toluenesulfonate (tosylate) in the presence of an organic base such as triethylamine. The new intermediate 4-methoxybenzyl 7β-[α-(2-chloroacetamido)thiazol-4-yl-α-methoxyimino]acetamido-3-methylenecepham-4-carboxylate thus obtained is isolated according to conventional procedures.

The 4-methoxybenzyl 7β-[α-(2-chloroacetamido)thiazol-4-yl-α-methoxyimino]acetamido-3-methylenecepham-4-carboxylate, which is another object of the invention is generally pure, but it may also contain a little amount (up to 10%) of the corresponding $\Delta^{3,4}$-reconjugation 3-methyl-3-cephem derivative. This $\Delta^{3,4}$-3-methyl compound is converted into the 3-exomethylene form during the subsequent step (ii).

The starting 4-methoxybenzyl 7β amino-3-methylenecepham-4-carboxylate of formula III may be obtained in good yields by treatment of the 4-methoxybenzyl 7β-phenylacetamido-3-chloromethyl-3-cephem-4-carboxylate, described in DE 3711625, with $PCl_5$.

In step (ii), the obtained 4-methoxybenzyl 7β-[α-(2-chloroacetamido)thiazol-4-yl-α-methoxyimino]acetamido-3-methylenecepham-4-carboxylate is reacted with the sulfenyl chloride of formula X—S—Cl, wherein X is as defined above, previously prepared by reaction of the corresponding disulfide X—S—S—X with chlorine. Any sulfenyl chloride, for example phenylsulfenyl chloride ($X=C_6H_5—$), benzylsulfenyl chloride ($X=C_6H_5—CH_2$) and their analogues substituted on the phenyl radical with, for example, methyl or methoxy groups may be used, but methanesulfenyl chloride ($CH_3SCl$) is particularly preferred. In practice, a solution of methanesulfenyl chloride (also known as methylsulfur monochloride) is prepared by mixing dimethyl disulfide ($CH_3—S—S—CH_3$) in anhydrous dichloromethane and $Cl_2$ dissolved in anhydrous ethyl acetate at a temperature of about 0° C. and a solution of 4-methoxybenzyl 7β-[α-(2-chloroacetamido)thiazol-4-yl-α-methoxyimino]acetamido-3-methylenecepham-4-carboxylate in anhydrous ethyl acetate is added thereto at the same temperature. The reaction mixture is let to stand 15–20 hours at 0–5° C. overnight and the 4-methoxybenzyl 7β-[α-(2-chloroacetamido)thiazol-4-yl-α-methoxyimino]acetamido-3-methylthio-3-chloromethylcepham-4-carboxylate thus obtained of formula V, wherein X is methyl and R" is 4-methoxybenzyl, is isolated according to conventional methods. If an amount of the starting material is present beside the desired compound, the product is used as such for the subsequent step (iii) is obtained. The 4-methoxybenzyl 7β-[α-(2-chloroacetamido)thiazol-4-yl-α-methoxyimino]acetamido-3-methylthio-3-chloromethylcepham-4-carboxylate is generally present as a mixture of the two diastereoisomers in a ratio of from 3/1 to 3.5/1.

The optical configuration of the carboxyl function —COOR" and of the 3-thio-3-halomethylcepham structure which are present in the cepham structure moiety of Scheme 1 is irrelevant according to this invention because all of the compounds III, IV, V and I are intermediates in the preparation of 3-cephem derivatives.

In step (iii) the 4-methoxybenzyl 7β-[α-(2-chloroacetamido)thiazol-4-yl-α-methoxyimino]acetamido-3-methylthio-3-chloromethylcepham-4-carboxylate (V) is reacted with a compound of formula Z-M, wherein Z is the residue of a nucleophilic compound selected from the group consisting of 2-furoylthio-, acetoxy and 1,2,5,6-tetrahydro-2-methyl-5,6-dioxo-1,2,4-triazin-3-ylthio radicals and M is hydrogen or an alkaline metal, preferably sodium or potassium. In practice, the diastereoisomeric mixture of 4-methoxybenzyl 7β-[α-(2-chloroacetamido)thiazol-4-yl-α-methoxyimino]acetamido-3-methylthio-3-chloromethylcepham-4-carboxylate, dissolved of in an organic solvent such as dichloromethane, dimethylformamide, dimethylacetamide is treated with the sodium of potassium salt of 2-thiofuroic acid, acetic acid or 1,2,5,6-tetrahydro-2-methyl-5,6-dioxo-1,2,4-triazin-3-thiol (2-methyl-5,6-dioxo-perihydro-1,2,4-triazine-3-thione) in an organic solvent or in water and the reaction may be carried out in a homogeneous or heterogeneous medium at a temperature of from 0 to 25° C. and the resulting diastereoisomeric mixture of the compound of formula I is isolated according to conventional techniques, for example by separating the phases and evaporating the organic solvent or by extracting the product and evaporating the solvent.

The diastereoisomeric mixture of the intermediate compound 4-methoxybenzyl 7β-[α-(2-chloroacetamido)thiazol-4-yl-α-methoxyimino]acetamido-3-methylthio-3-chloromethylcepham-4-carboxylate (formula V of Scheme 1) may be further submitted to an oxidation with nascent oxygen, for example by treatment with a peracid such as m-chloroperbenzoic acid in an organic solvent such as dichloromethane) dimethyl formamide, dimethyl acetamide at a temperature of from −5° C. to +5° C. to give 4-methoxybenzyl 7β-[α-(2-chloroacetamido)thiazol-4-yl-α-methoxyimino]acetamido-3-chloromethyl-3-cephem-4-carboxylate. This compound may be treated with the sodium or potassium salt of 2-thiofuroic acid, acetic acid or 1,2,5,6-tetrahydro-2-methyl-5,6-dioxo-1,2,4-triazin-3-thiol (2-methyl-5,6-dioxo-perihydro-1,2,4-triazine-3-thione) as illustrated above and converted into a direct precursor of ceftiofur, cefotaxime and ceftriaxone, respectively, that may be deprotected according to conventional methods and thus converted into ceftiofur, cefotaxime ad ceftriaxone, respectively. This conversion occurs according to Scheme 2 below.

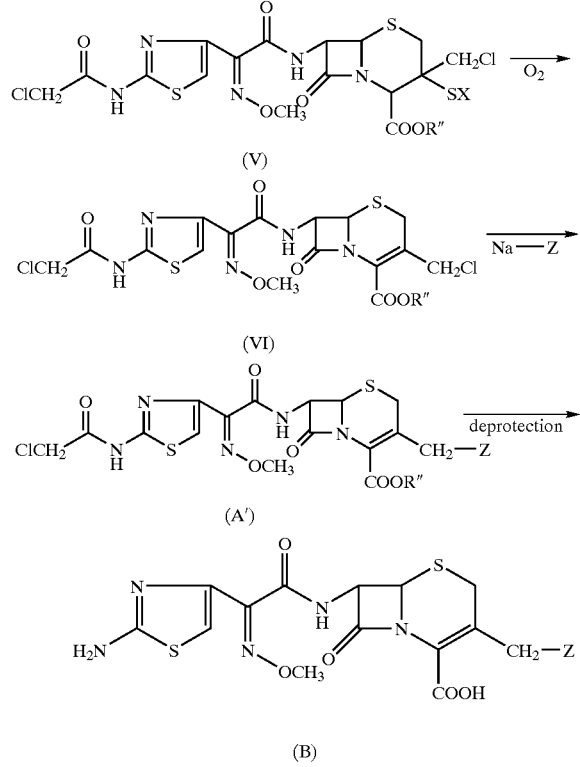

wherein R'', X and Z are as defined above.

Alternatively, the diastereoisomeric mixture of the compound of formula I of Scheme 1 may be submitted to an oxidation with nascent oxygen, for example by treatment with a peracid such as m-chloroperbenzoic acid in an organic solvent such as dichloromethane, dimethyl formamide, dimethyl acetamide at a temperature in the range of from −5° C. to +5° C. to give a compound of formula VII. This compound must be submitted to a reduction of the 1-oxide function by $SnCl_2$ in order to isolate the compound of formula A', which, by deprotection of the aminothiazolyl and of the carboxyl functions, gives ceftiofur, cefotaxime or ceftriaxone, represented by the compounds B. This conversion occurs according to Scheme 3 below.

The deprotection of the carboxyl group is made according to the methods known in the art. More particularly, the 4-methoxybenzyl group is removed for example by formic acid, as described by G. C. Stelakatos et al. in J. Chem. Soc. C, 1970, page 964 or by trifluoroacetic acid and phenol or anisole, as described by F. H. C. Stewart in Aust. J. Chem. 1968, 21, page 2543, by H. Tanaka et al. in Tetrahedron Lett. 1990, 31, page 6661 or by S. Torii et al. in J. Org Chem. 1991, 56, 3633.

The deprotection of the 2-aminothiazolyl group is also made according to known methods. In particular, the chloroacetyl group is cleaved by treatment with thiourea as described for example in by M. Masaki et al. in J. Am Chem Soc 1968, 90, page 4508, by J. E. Baldwin et al. in Tetrahedron, 1986, 42, page 3097 or by T. Allmendinger et al. in Helv. Chim. Acta 1988, 71, 395.

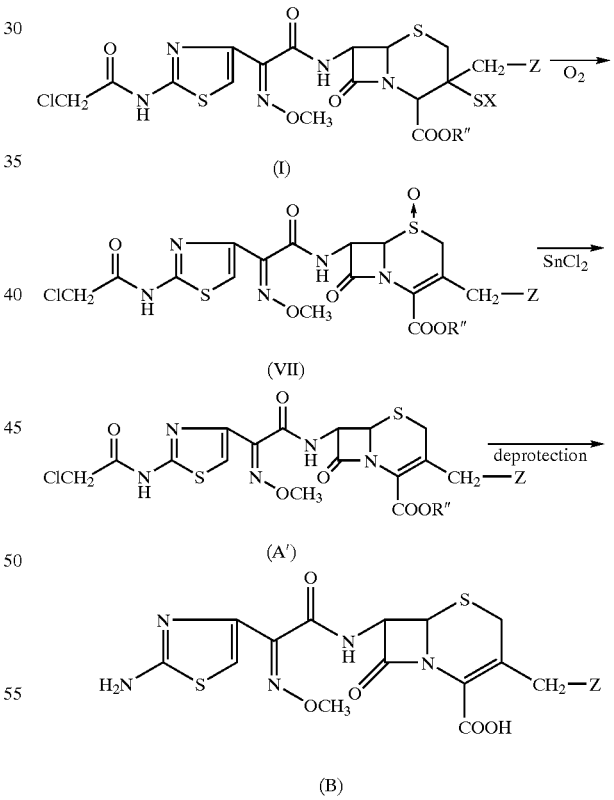

Finally, according to Scheme 2 or Scheme 3, it is also possible to prepare cefotaxime (formula B, Z=$CH_3$—CO—O—) or the precursor thereof of formula A' in which Z is $CH_3$—CO—O—, and to convert it into ceftriaxone or into a precursor thereof of formula A' in which Z is 1,2,5,6-tetrahydro-2-methyl-5,6-dioxo-1,2,4-triazin-3-ylthio, by reacting said cefotaxime or said precursor thereof with 2-methyl-5,6-dioxo-perihydro-1,2,4-triazine-3-thione in the presence of boron trifluoride in an organic solvent such as dichloromethane or acetonitrile.

In the above described process, the chloroacetyl group is illustrated as N-protecting group of the 2-aminothiazolyl radical and the 4-methoxybenzyl group is illustrated as protecting group of the carboxyl function, but any protecting group which is stable in acidic medium is suitably used in the process of the invention In particular, any N-protective group stable in an acidic medium, i.e. a protective group which is not removed under acidic conditions due to a pH of from 1 to 6, in particular of from 2 to 4, considered in an aqueous medium, as illustrated by T. W. Greene and P. G. M. Wuts in "Protective Groups in Organic Synthesis", 3$^{rd}$ Edition, 1999, John Wiley & Sons may be used instead of the chloroacetyl group. Analogously, any ester group stable in acidic medium, i.e. a protective group of the carboxyl function which is not removed under acidic conditions due to a pH of from 1 to 6, in particular of from 2 to 4, considered in an aqueous medium, as illustrated by T. W. Greene and P. G. M Wuts in the above-cited book may be successfully used instead of the 4-methoxybenzyl group In the above-illustrated process, the compounds of formulas I and V are key intermediates in the preparation of the compounds of formula B.

Thus, according to an embodiment of the present invention the compound of formula V obtained at the end of step (ii) is further reacted and submitted to reaction steps consisting of (iii') submitting said compound of formula V to an oxidation with nascent oxygen, advantageously with a peracid such as m-chloroperbenzoic acid, (iv') treating the compound thus obtained of formula VI with a compound of formula M-Z, wherein M is an alkaline metal and Z is the residue of a nucleophilic compound selected from the group consisting of the 2-furoylthio, acetoxy and 1,2,5,6-tetrahydro-2-methyl-5,6-dioxo-1,2,4-triazin-3-ylthio radicals; and (v') deprotecting the compound of formula A' thus obtained to obtain a compound of formula B.

Also the 4-methoxybenzyl 7β-[α-(2-chloroacetamido)thiazol-4-yl-α-methoxyimino]acetamido-3-chloromethyl-3-cephem-4-carboxylate of formula VI is a new compound which represent a further object of the invention.

According to another embodiment of the present invention, the compound of formula I obtained at the end of step (iii) is farther reacted and submitted to reaction steps consisting of (iv) submitting said compound of formula I to an oxidation with nascent oxygen, advantageously with a peracid such as m-chloroperbenzoic acid:

(v) submitting the compound of formula VII thus obtained to a reduction, for example with stannous chloride;

(vi) deprotecting the compound of formula B thus obtained to obtain a compound of formula A.

Another embodiment of the present invention provides a process for preparing cefotaxime which comprises (a) reacting a functional derivative of the α-(2-chloroacetamido)thiazol-4-yl-α-methoxyiminoacetic acid of formula II

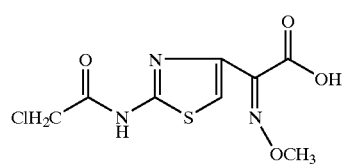

with a 7β-amino-3-methylenecepham-4-carboxylic acid derivative of formula III

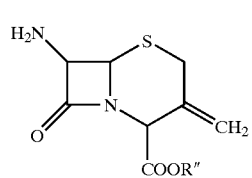

wherein R" is 4-methoxybenzyl, or with an addition salt thereof;

(b) treating the corresponding 4-methoxybenzyl 7β-[α-(2-chloroacetamido)thiazol-4-yl-α-methoxyimino]acetamido-3-methylenecepham-4-carboxylate thus obtained of formula IV

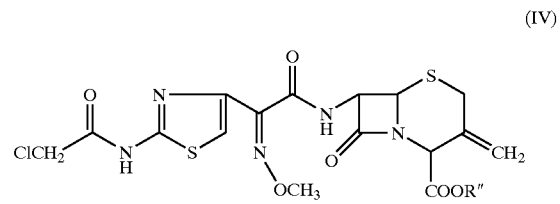

wherein R" is 4-methoxybenzyl, with a S-chloromercaptan of formula X—S—Cl, in which X is as defined above; and (c) reacting the corresponding 7β-[α-(2-chloroacetamido)thiazol-4-yl-α-methoxyimino]acetamido-3-thio-3-chloromethyl-4-carboxylic acid derivative thus obtained of formula V

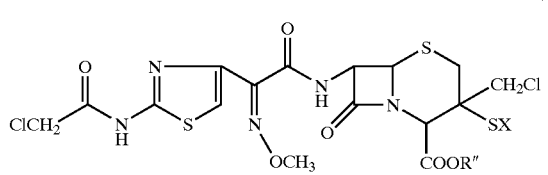

wherein R" and X are as defined above, with sodium or potassium acetate;

(d) submitting the compound thus obtained of formula Ia

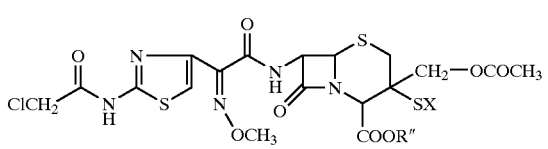

wherein X and R" are as defined above, to an oxidation with a peracid;

(e) submitting the compound thus obtained of formula VII (VIIa)

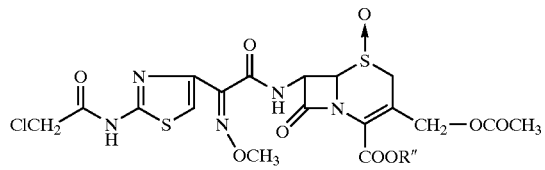

wherein R" is as defined above, to a reduction with stannous chloride; and (f) deprotecting the compound thus obtained of formula VIIIa (VIIIa)

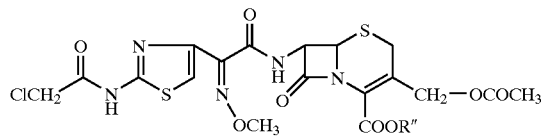

wherein R" and Z are as defined above, to obtain cefotaxime.

In step (b), the preferred S-chloromercaptan is methane sulfenyl chloride (X—S—Cl, X being methyl). In step (d), the preferred peracid is m-chloroperbenzoic acid. The deprotection of compound VIIIa is preferably carried out by first treating said compound VIIIa with an agent capable of cleaving the 4-methoxybenzyl radical, for example with formic acid (J. Chem. Soc. 1970, 964) or with trifluoroacetic acid and anisole or phenol (Aust. J. Chem. 1968, 21, 2543; Tetrahedron Lett. 1990, 31, 6661; J. Org. Chem. 1991, 56, 3633), and then cleaving the N-chloroacetyl group for example by thiourea (J. Chem. Soc. 1968, 90, 4508; Tetrahedron, 1986, 42, 3097; Helv. Chim. Acta 1988, 71, 395).

The compound VIIIa obtained at the end of step (e), i.e. the diprotected cefotaxime may be further treated and reacted with 2-methyl-5,6-dioxo-perihydro-1,2,4-triazine-3-thione in the presence of $BF_3$ to isolate a compound of formula VIIIb (VIIIb)

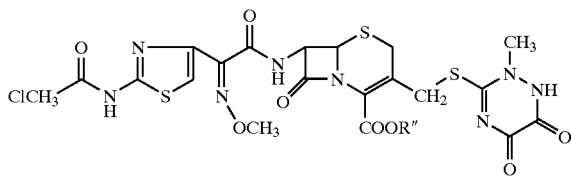

wherein R" is 4-methoxybenzyl, which is further submitted to a double deprotection to isolate ceftriaxone. Said deprotection is carried out as set forth above, for example by submitting compound VIIIb, to a reaction with formic acid, whereby the 4-methoxybenzyl group represented by R" is removed and to a subsequent reaction of the corresponding free acid thus obtained with thiourea, whereby the N-chloroacetyl group is cleaved.

It is also possible to treat cefotaxime with 2-methyl-5,6-dioxo-perihydro-1,2,4-triazine-3-thione in the presence of $BF_3$ to isolate ceftriaxone straightforwardly.

The key intermediates of formulas V and I are novel compound which represent a further embodiment of the present invention, Thus, it is another object of the present invention to provide novel 3-disubstituted cepham derivatives of formula I'

(I')

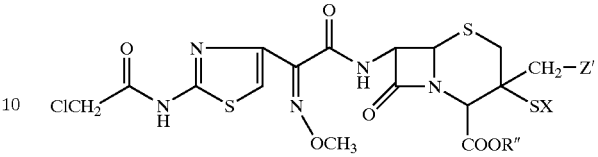

wherein R" is 4-methoxybenzyl, Z' is a chlorine atom or the residue of a nucleophilic compound selected from the group consisting of the 2-furoylthio, acetoxy, and 1,2,5,6-tetrahydro-2-methyl-5,6-dioxo-1,2,4-triazin-3-ylthio radicals and X is a residue of a thioether. As a residue of a thioether, the methyl group is particularly preferred.

The following examples illustrate the invention without, however, limiting it.

Preparation I 2-(2-chloroacetamidothiazol-4-yl)-2-syn-methoxyiminoacetic acid

To a suspension of 20 g of α-(2-aminothiazol-4-yl)-α-methoxyiminoacetic acid in 60 ml of anhydrous tetrahydrofuran, 37.2 ml of dimethylacetamide are added under stirring, then the mixture is cooled to −15° C. and 15.93 ml of monochloroacetyl chloride are added thereinto by keeping the temperature not higher than −5° C. After a 4-hour stirring 200 ml of distilled water are added, the mixture is extracted twice with 200 ml of ethyl acetate, washed 4 times with 100 ml of water, dried on sodium sulfate and evaporated under reduced pressure. The solid residue is suspended in 150 ml of ethyl acetate and 100 ml of n-hexane the mixture is let to stand 5 hours under vigorous stirring and the suspended solid is filtered to give 17.5 g of practically pure 2-(2-chloroacetamidothiazol-4-yl)-2-syn-methoxyiminoacetic acid.

Preparation II

4-Methoxybenzyl 7β-amino-3-methylenecepham-4-carboxylate

To a previously cooled (−15° C.) solution of 5 g of 4-methoxybenzyl 7β-phenylacetamido-3-methylenecepham-4-carboxylate in 200 ml of anhydrous dichloromethane, 8.9 ml of anhydrous pyridine and, subsequently, 7.3 g of $PCl_5$ are added under stirring, and stirring is continued for 1 hour at −15° C. The reaction mixture is cooled to −30° C., 55.4 ml of absolute methanol are added thereinto, the mixture is stirred 90 minutes at −15° C. then 60 minutes at 0° C. and finally 60 minuts at 25° C. To the resulting mixture, 200 ml of a 0.5 M solution of $K_2HPO_4$ are added, the the pH is adjusted to bout 2 by addition of 5% $H_3PO_4$. The mixture is let to stand 30 minutes under stirring at 25° C., then the organic phase is separated, the organic one is extracted twice with dichloromethane and the collected organic phases are dried over sodium sulfate and concentrated under reduced pressure. The obtained oily residue is dissolved in 70 ml of ethyl acetate, the solution is cooled to 0° C. and treated first with a solution of 3.15 g of p-toluene sulfonic acid monohydrate in 70 ml of ethyl acetate, then with 70 ml of diethyl ether. After standing overnight at 4° C., the precipitate is filtered to give 3.92 g of practically pure (thin layer chromatography, eluent ethyl acetate/n-hexane 7/3, $R_f$=0.20) 4-methoxybenzyl 7β-amino-3-methylenecepham-4-carboxylate p-toluenesulfonic acid addition salt.

EXAMPLE 1

To solution, under stirring and nitrogen atmosphere at 25° C., of 548 mg of 2-(2-chloroacetamidothiazol-4-yl)-2-syn-methoxyiminoacetic acid in 50 ml of anhydrous dichloromethane, 1 g of 4-methoxybenzyl 7βamino-3-methylenecepham-4-carboxylate p-toluenesulfonic acid addition salt and 137 μl of triethylamine are added. The mixture is cooled to 0° C., then 874 mg of BOP reagent is added thereinto and, after one hour stirring, its temperature is brought to 25° C. and a further volume of 137 μl of triethylamine are added thereinto. After a 24-hour stirring at 25° C., the mixture is washed with water, with 0.5 HCl and with a saturated solution of NaHCO₃, then it is dried over sodium sulfate and concentrated under reduced pressure to give 1.13 g of 4-methoxybenzyl 7β-[α-(2-chloroacetamido) thiazol-4-yl-α-methoxyimino]acetamido-3-methylenecepham-4-carboxylate. A purification by flash chromatography (eluent diethyl ether/dichloromethane 1/4 gives a purified product that, under the conditions of this preparation, contains about 10% of the corresponding 4-methoxybenzyl 7β-[α-(2-chloroacetamido)thiazol-4-yl-α-methoxyimino]acetamido-3-methyl-3-cephem-4-carboxylate.

EXAMPLE 2

To a solution of 400 mg of the 4-methoxybenzyl 7β-[α-(2-chloroacetamido)thiazol-4-yl-α-methoxyimino] acetamido-3-methylenecepham-4-carboxylate obtained in Example 1 in 10 ml of anhydrous dichloromethane, previously cooled to 0° C., a solution of methyl sulfenyl chloride (prepared aside by mixing 30 μl of dimethyl disulfide and 204 μl of a 1.65M solution of chlorine in ethyl acetate with 2.5 ml of anhydrous dichloromethane at 0° C. and by keeping the solution at 0° C. under stirring for one hour) is added dropwise slowly, then the mixture is stirred at the same temperature for 90 minutes, let to stand at 0–5° C. for 16–18 hours and finally treated with 5 ml of a 1M solution of Na₂S₂O₃. After a 15-minute stirring, the phases are separated, the aqueous one is extracted twice with dichloromethane and the collected organic phases are dried over anhydrous sodium sulfate and concentrated under reduced pressure to give 387 mg of a diastereoisomeric mixture 3.3/1 of 4-methoxybenzyl 7β-[α-(2-chloroacetamido)thiazol-4-yl-α-methoxyimino]acetamido-3-methylthio-3-chloromethylcepham-4-carboxylate containing some residual, starting 4-methoxybenzyl 7β-[α-(2-chloroacetamido)thiazol-4-yl-α-methoxyimino]acetamido-3-methylenecepham-4-carboxylate.

¹H-NMR (300 MHz, CDCl₃, 25° C.), δ(ppm), the differences being in italic.
More Abundant Diastereoisomer:

10.15 (1H, br, s, NH—Ar); 7.41 (1H, d, J=9.1 Hz, NH—C-7); 7.36 (1H, s, H-5'); 7.30 (2H, d, J=8.4 Hz, 2H-14); 6,92 (2H, d, J=8.4 Hz, 2H-15); 5.77 (1H, dd, J=9.1, 4.4 Hz, H-7); 5.40 (1H, d, J=4.4 Hz-H-8); 5.13 and 5.11 (2H, system AB, J=11.6 Hz, 2H-12); 4.47 (1H, s, H-4); 4.26 (2H, br, s, 2H-9'); 4.08 (3H, s, NOCH₃); 3.83 (3H, s, ArOCH₃); 3.70 and 3.47 (2H, system AB, J=12.2 Hz, 2H-9); 3.67 and 2.76 (2H, system AB, J=14.5 Hz, 2H-2), 2.00 (3H, s, SCH₃).
Less Abundant Diastereoisomer:

10.15 (1H, br, s, NH—Ar); 7.41 (1H, d, J=9.1 Hz, NH—C-7); 7.36 (1H, s, H-5'); 7.30 (2H, d, J=8.4 Hz, 2H-14); 6,92 (2H, d, J=8.4 Hz, 2H-15); 5.77 (1H, dd, J=9.1, 4.4 Hz, H-7); 5.38 (1H, d, J=4.4 Hz-H-8); 5.13 and 5.11 (2H, system AB, J=11.6 Hz, 2H-12); 4.51 (1H, s, H-4); 4.26 (2H, br, s, 2H-9'); 4.08 (3H, s, NOCH₃); 3.83 (3H, s ArOCH₃); 3.72 and 3.44 (2H, system AB, J=12.2 Hz, 2H-9); 3.64 and 2.83 (2H, system AB, J=14.4 Hz, 2H-2), 2.03 (3H, s, SCH₃).

EXAMPLE 3

To a solution of 0.005 mole of a diastereoisomeric mixture 3.3/1 of 4-methoxybenzyl 7β-[α-(2-chloroacetamido) thiazol-4-yl-α-methoxyimino]acetamido-3-methylthio-3-chloromethylcepham-4-carboxylate in 14 ml of dimethyl formamide, 0.075 mole of sodium acetate and 0.005 mole of acetic acid are added. The mixture is cooled, then it is poured into a water/ice mixture and the mixture thus obtained is extracted twice with 50+25 ml of ethyl acetate. The collected organic phases are washed with a 5% aqueous solution of NaHCO₃, then with water and finally dried over anhydrous sodium sulfate. The yellowish oil obtained as a residue is purified by flash chromatography on silica gel (toluene/ethyl acetate 5/1) to obtain a diastereoisomeric mixture 3.3/1 of 4-methoxybenzyl 7β-[α-(2-chloroacetamido)thiazol-4-yl-α-methoxyimino]acetamido-3-methylthio-3-acetoxymethylcepham-4-carboxylate as a white solid. Yield:. 85% of the theoretical.

EXAMPLE 4

To a solution of 0.0036 mole of a diastereoisomeric mixture 3.3/1 of 4-methoxybenzyl 7β-[α-(2-chloroacetamido)thiazol)-4-yl-α-methoxyimino]acetamido-3-methylthio-3-chloromethylcepham-4-carboxylate in 125 ml of dichloromethane, a solution of 0.053 mole of 1,2,5, 6-tetrahydro-2-methyl-5,6-dioxo-1,2,4-triazine-3-thiol (2-methyl-5,6-dioxo-hexahydro-1,2,4-triazine-3-thione) sodium salt in 62.5 ml of water is added. After addition of 0.75 g of tetra-n-butylammonium bromide, the obtained mixture is stirred 6 hours at 20–25° C., then the phases are separated, the organic one is collected and concentrated under vacuum (oil pump). The residue is taken up with 15 ml of methanol, filtered and dried to give a diastereoisomeric mixture 3.3/1 of 4-methoxybenzyl 7β-[α-(2-chloroacetamido)thiazol-4-yl-α-methoxyimino]acetamido-3-methylthio-3-[(1,2,5,6-tetrahydro-2-methyl-5,6-dioxo-1, 2,4-triazin-3-yl)thio]cepham-4-carboxylate as a white solid Yield 77%.

EXAMPLE 5

To a mixture of 0.20 mmol of the diastereoisomeric mixture of 4-methoxybenzyl 7β-[α-(2-chloroacetamido) thiazol-4-yl-α-methoxyimino]acetamido-3-methylthio-3-chloromethylcepham-4-carboxylate obtained as described in Example 2 and of 0.46 mmol of m-chloroperbenzoic acid in 1.5 ml of dichloromethane, previously stirred for 30 minutes at 0° C., 10 ml of dichloromethane are added, then it is washed with a 10% aqueous solution of sodium metabisulfite, then with an aqueous solution of sodium bicarbonate and finally with water. The solution thus obtained, previously dried over anhydrous sodium sulfate, is concentrated and the residue is taken up with 10 ml of acetone. The solution thus obtained is concentrated and the residue is chromatographed on silica gel (eluent: ethyl acetate) to give 4methoxybenzyl 7β-[α-(2-chloroacetamido) thiazol-4-yl-α-methoxyimino]acetamido-3-chloromethyl-3-cephem-4-carboxylate in a 75% yield.

EXAMPLE 6

By operating as described in Example 5, starting from 0.20 mmol of 4-methoxybenzyl 7β-[α-(2-chloroacetamido) thiazoi-4-yl-α-methoxyimino]acetamido-3-methylthio-3-acetoxymethylcepham-4-carboxylate, as obtained in Example 3, and 0.46 mmol of m-chloroperbenzoic acid, 4-methoxybenzyl 7β-[α-(2-chloroacetamido)thiazol-4-yl-α-methoxyimino]acetamido-3-acetoxymethyl-3-cephem-4-carboxylate 1-oxide is obtained in a 80% yield.

I claim:

1. A process for the preparation of a 3-disubstituted cepham-4-carboxylic acid derivative of formula I

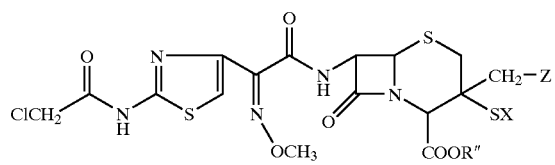

(I)

wherein R" is 4-methoxybenzyl, X is the residue of a thioether selected from the group consisting of phenyl; phenyl substituted on the benzene ring with a methyl or methoxy group; benzyl; benzyl substituted on the benzene ring with a methyl or methoxy group; and methyl radicals and Z is the residue of a nucleophilic compound selected from the group consisting of 2-furoylthio, acetoxy and 1,2,5,6-tetrahydro-2-methyl-5,6-dioxo-1,2,4-triazin-3-ylthio radicals, which process comprises (i) reacting a functional derivative of the α-(2-chloroacetamido)thiazol-4-yl-α-methoxyiminoacetic acid of formula II

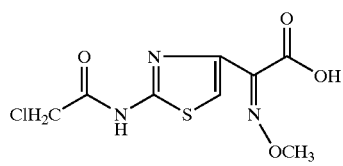

(II)

selected from the group consisting of acid halides, anhydride, mixed anhydrides, active esters and an acid activated with a reagent selected from the group consisting of dicyclohexylcarbodiimide, mercaptobenzotriazole and benzotriazol-1-yloxy-tris(dimethylamino) phosphonium hexafluorophosphate, with a 7β-amino-3-methylenecepham-4-carboxylic acid derivative of formula III

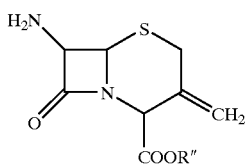

(III)

wherein R" is 4-methoxybenzyl, or with an addition salt thereof;

(ii) treating the corresponding 4-methoxybenzyl 7β-[α-(2-chloroacetamido)thiazol-4-yl-α-methoxyimino] acetamido-3-methylenecepham-4-carboxylate thus obtained of formula IV

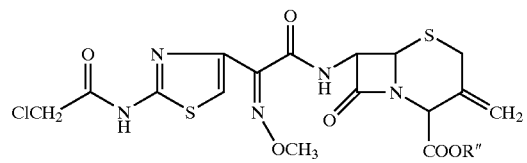

(IV)

wherein R" is 4-methoxybenzyl, with a S-chloromercaptan of formula X—S—Cl, in which X is as defined above; and (iii) reacting the corresponding 4-methoxybenzyl 7β-[α-(2-chloroacetamido)thiazol-4-yl-α-methoxyimino] acetamido-3-thio-3chloromethylcepham-4carboxylate thus obtained of formula V

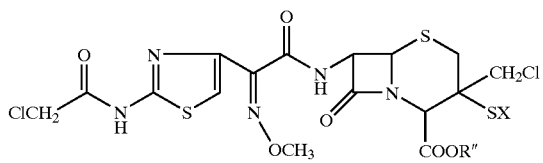

(V)

wherein R" and X are as defined above, with a compound of formula M-Z, in which M is an alkaline metal or a hydrogen atom and Z is the residue of a nucleophilic compound selected from the group consisting of the 2-furoylthio, acetoxy and 1,2,5,6-tetrahydro-2-methyl-5,6-dioxo-1,2,4-triazin-3-ylthio radicals.

2. A process according to claim 1, wherein X is a methyl group.

3. A process according to claim 1, wherein the compound of formula I obtained at the end of step (iii) is further reacted and submitted to reaction steps consisting of (iv) submitting said compound of formula I to an oxidation with a peracid;

(v) submitting the compound thus obtained of formula VII

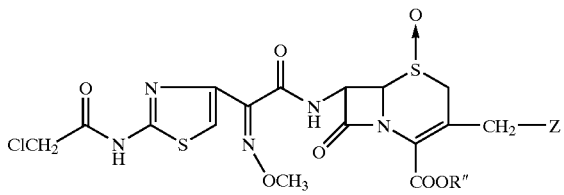

(VII)

wherein R" is 4-methoxybenzyl and Z is the residue of a nucleophilic compound selected from the group consisting of the 2-furoylthio, acetoxy and 1,2,5,6-tetrahydro-2-methyl-5,6-dioxo-1,2,4-triazin-3-ylthio radicals, to a reduction with stannous chloride;

(vi) deprotecting the compound thus obtained of formula A'

(A')

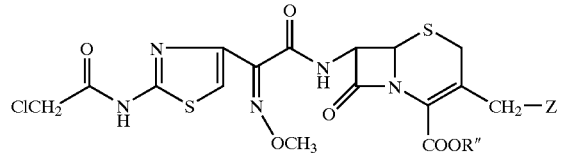

wherein R" and Z are as defined above, to obtain a compound of formula B (B)

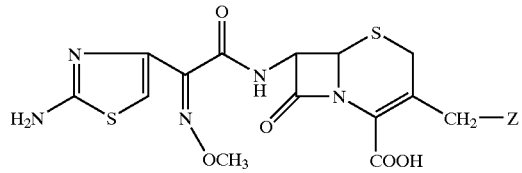

wherein Z is as defined above.

4. A process according to claim 3, wherein the starting material has the formula I, in which X is methyl.

5. A process according to claim 4, wherein the peracid used in step (iv) is m-chloroperbenzoic acid.

6. A process according to claim 5, wherein the deprotection of step (vi) consists of a reaction of compound A' with formic acid, whereby the 4-methoxybenzyl group represented by R" is removed and of a subsequent reaction of the corresponding free acid thus obtained with thiourea, whereby the N-chloroacetyl group is cleaved.

7. A process for preparing cefotaxime which comprises (a) reacting a functional derivative of the α-(2-chloroacetamido)thiazol-4-yl-α-methoxyiminoacetic acid of formula II (II)

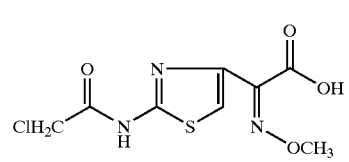

selected from the group consisting of acid halides, anhydride, mixed anhydrides, active esters and an acid activated with a reagent selected from the group consisting of dicyclohexylcarbodiimide, mercaptobenzotriazole and benzotriazol-1-yloxy-tris(dimethylamino) phosphonium hexafluorophosphate, with a 7β-amino-3-methylenecepham-4-carboxylic acid derivative of formula III (III)

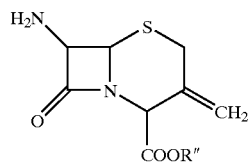

wherein R" is 4-methoxybenzyl, or with an addition salt thereof;

(b) treating the corresponding 4-methoxybenzyl 7β-[α-(2-chloroacetamido)thiazol-4-yl-α-methoxyimino] acetamido-3-methylenecepham-4-carboxylate thus obtained of formula IV (IV)

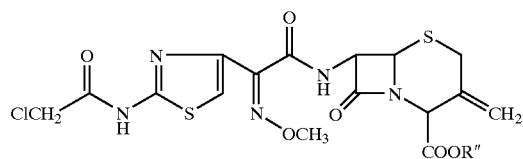

wherein R" is 4-methoxybenzyl, with a S-chloromercaptan of formula X—S—Cl, in which X is the residue of a thioether selected from the group consisting of phenyl; phenyl substituted with a methyl or methoxy group; benzyl; benzyl substituted with a methyl or methoxy group; and methyl radicals;

(c) reacting the corresponding 7β-[α-(2-chloroacetamido) thiazol-4-yl-α-methoxyimino]acetamido-3-thio-3chloromethyl-4-carboxylic acid derivative thus obtained of formula V (V)

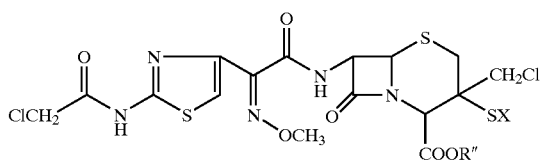

wherein R" and X are as defined above, with sodium or potassium acetate;

(d) submitting the compound thus obtained of formula Ia (Ia)

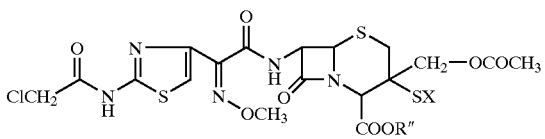

wherein X and R" are as defined above, to an oxidation with a peracid;

(e) submitting the compound thus obtained of formula VII (VIIa)

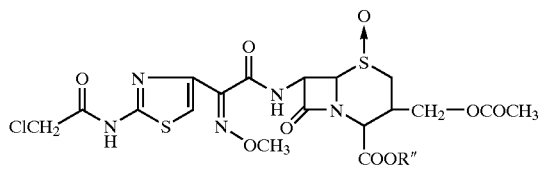

wherein R" is as defined above, to a reduction with stannous chloride; and (f) deprotecting the compound thus obtained of formula VIIIa

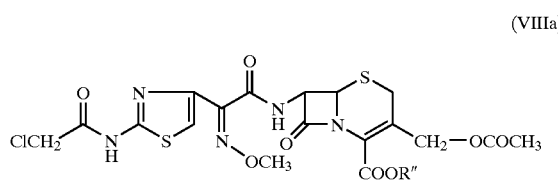
(VIIIa)

wherein R" and Z are as defined above, to obtain cefotaxime.

8. A process according to claim 7, wherein, in step (b) the S-chloromercaptan of formula X—S—Cl is methanesulfenyl chloride of formula X—S—Cl wherein X is methyl.

9. A process according to claim 8, wherein the peracid used in step (d) is m-chloroperbenzoic acid.

10. A process according to claim 8, wherein the deprotection of step (f) consists of a reaction of compound VIIIa with formic acid, whereby the 4-methoxybenzyl group represented by R" is removed and of a subsequent reaction of the corresponding free acid thus obtained with thiourea, whereby the N-chloroacetyl group is cleaved.

11. The process of claim 7, wherein said cefotaxime is further treated and reacted with 2-methyl-5,6-dioxoperihydro-1,2,4-triazine-3-thione in the presence of $BF_3$ to isolate ceftriaxone.

12. 4-Methoxybenzyl 7β-[α-(2-chloroacetamido)thiazol-4yl-α-methoxyimino]acetamido-3-methylenecepham-4-carboxylate of formula IV

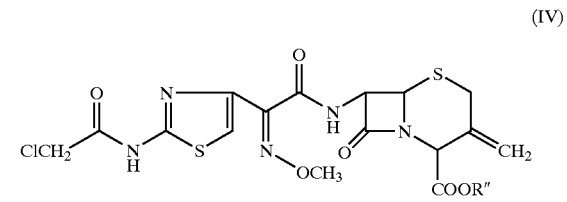
(IV)

wherein R" is 4-methoxybenzyl.

13. A 3,3-disubstituted cepham derivative of formula I'

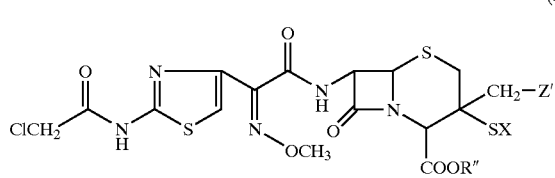
(I')

wherein R" is 4-methoxybenzyl, Z' is a chlorine atom or a radical selected from the group consisting of the 2-furoylthio, acetoxy, and 1,2,5,6-tetrahydro-2-methyl-5,6-dioxo-1,2,4-triazin-3-ylthio radicals and X is the residue of a thioether selected from the group consisting of phenyl; phenyl substituted on the benzene ring with a methyl or methoxy group; benzyl; benzyl substituted on the benzene ring with a methyl or methoxy group; and methyl radicals.

14. A 3,3-disubstituted cepham derivative according to claim 13 having the formula I' wherein X is methyl.

15. 4-Methoxybenzyl 7β[α-(2-chloroacetamido)thiazol-4-yl-α-methoxyimino]acetamido-3-chloromethyl-3cephem-4carboxylate of formula VI

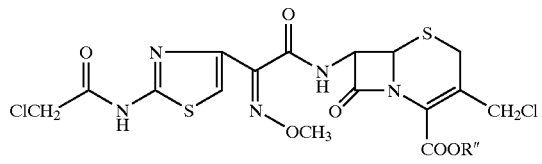
(VI)

wherein R" is 4-methoxybenzyl.

16. A process for the preparation of compound of formula (B)

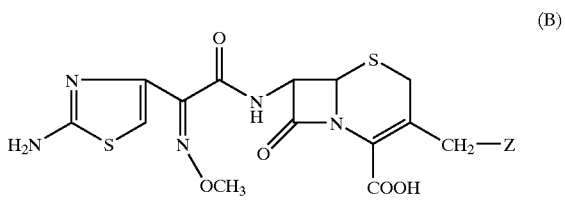
(B)

wherein Z is the residue of a nucleophilic compound selected from the group consisting of 2-furoylthio, acetoxy and 1,2,5,6-tetrahydro-2-methyl-5,6-dioxo-1,2,4-triazin-3-ylthio radicals, which process comprises (i) reacting a functional derivative of the α-(2-chloroacetamido)thiazol-4-yl-α-methoxyiminoacetic acid of formula II

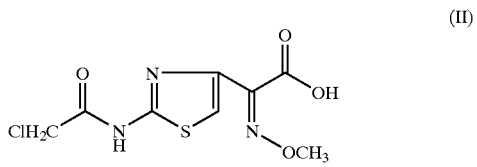
(II)

selected from the group consisting of acid halides, anhydride, mixed anhydrides, active esters and an acid activated with a reagent selected from the group consisting of dicyclohexylcarbodiimide, mercaptobenzotriazole and benzotriazol-1-yloxy-tris(dimethylamino) phosphonium hexafluorophosphate, with a 7β-amino-3-methylenecepham-4-carboxylic acid derivative of formula III

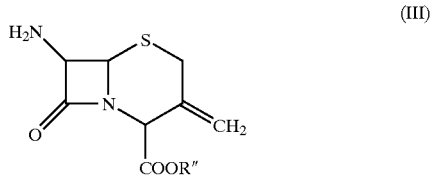
(III)

wherein R" is 4-methoxybenzyl, or with an addition salt thereof;

(ii) treating the corresponding 4-methoxybenzyl 7β-[α-(2-chloroacetamido)thiazol-4-yl-α-methoxyimino] acetamido-3-methylenecepham-4-carboxylate thus obtained of formula IV (IV)

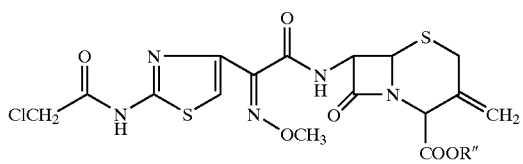

wherein R" is 4-methoxybenzyl, with a S-chloromercaptan of formula X—S—Cl, in which X is a residue of a thioether selected from the group consisting of phenyl; phenyl substituted on the benzene ring with a methyl or methoxy group; benzyl; benzyl substituted on the benzene ring with a methyl or methoxy group; and methyl radicals;

(iii') submitting the compound thus obtained of formula V (V)

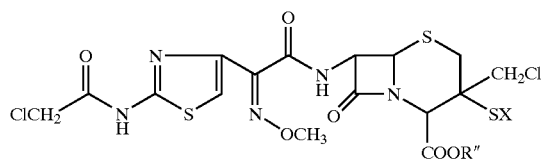

wherein R" and X are as defined above, to an oxidation with m-chloroperbenzoic acid;

(iv') treating the compound thus obtained of formula VI (VI)

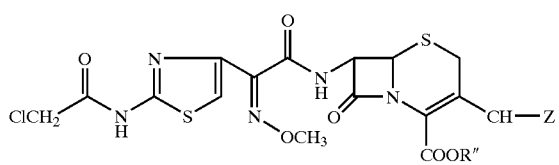

with a compound of formula M-Z, wherein M is an alkaline metal and Z is as defined above; and (v') deprotecting the compound thus obtained of formula A'

(A')

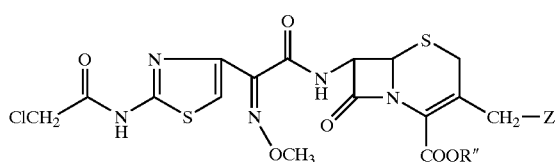

to isolate the compound of formula B.

17. The process according to claim 16 wherein in the formula X—S—Cl, X is a methyl group.

18. A process for preparing ceftriaxone, which comprises (a) reacting a functional derivative of the α-(2-chloroacetamido)thiazol-4-yl-α-methoxyiminoacetic acid of formula II (II)

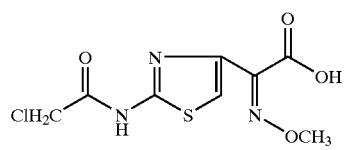

selected from the group consisting of acid halides, anhydride, mixed anhydrides, active esters and an acid activated with a reagent selected from the group consisting of dicyclohexylcarbodiimide, mercaptobenzotriazole and benzotriazol-1-yloxy-tris(dimethylamino)phosphonium hexafluorophosphate, with a 7β-amino-3-methylenecepham-4-carboxylic acid derivative of formula III (III)

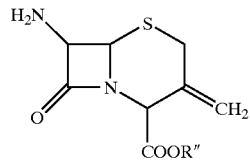

wherein R" is 4-methoxybenzyl, or with an addition salt thereof;

(b) treating the corresponding 4-methoxybenzyl 7β-[α-(2-chloroacetamido)thiazol-4-yl-α-methoxyimino]acetamido-3-methylenecepham-4-carboxylate thus obtained of formula IV (IV)

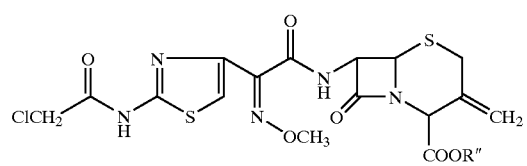

wherein R" is 4-methoxybenzyl, with a S-chloromercaptan of formula X—S—Cl, in which X is the residue of a thioether selected from the group consisting of phenyl; phenyl substituted with a methyl or methoxy group; benzyl; benzyl substituted with a methyl or methoxy group; and methyl radicals;

(c) reacting the corresponding 7β-[α-(2-chloroacetamido)thiazol-4-yl-α-methoxyimino]acetamido-3-thio-3-chloromethyl-4-carboxylic acid derivative thus obtained of formula V (V)

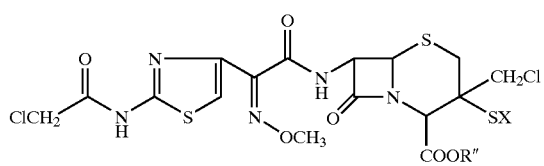

wherein R" and X are as defined above, with sodium or potassium acetate;

(d) submitting the compound thus obtained of formula Ia (Ia)

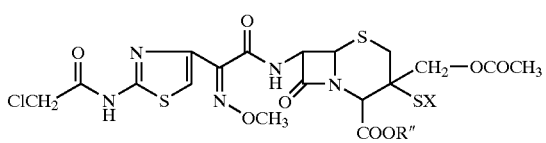

wherein X and R" are as defined above, to an oxidation with a peracid;

(e) submitting the compound thus obtained of formula VII

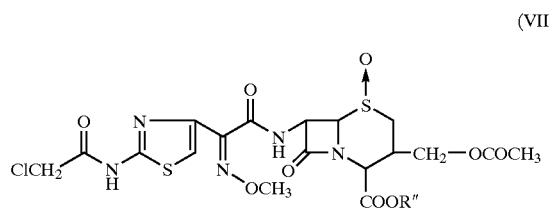
(VIIa)

wherein R" is as defined above, to a reduction with stannous chloride;

(f') treating the compound thus obtained of formula VIIIa

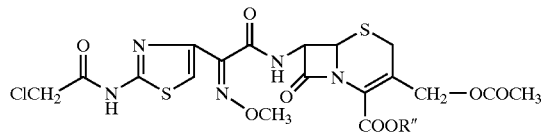
(VIIIa)

with 2-methyl-5,6-dioxo-perihydro-1,2,4-triazine-3-thione in the presence of BF$_3$; and (g') deprotecting the compound of formula VIIIb

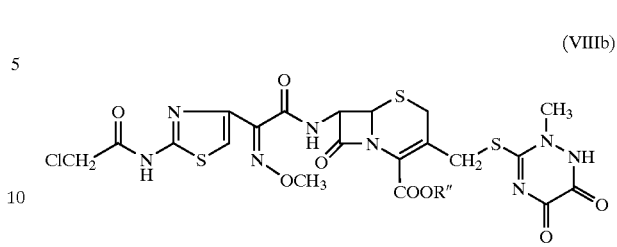
(VIIIb)

wherein R" is 4-methoxybenzyl, to isolate ceftriaxone.

19. The process of claim 18, wherein in step (g'), said deprotection is by reacting a compound VIIIb with formic acid, whereby the 4-methoxybenzyl group represented by R" is removed and thereafter reacting the corresponding free acid thus obtained with thiourea, whereby the N-chloroacetyl group is cleaved.

* * * * *